United States Patent
Wasmoen et al.

(10) Patent No.: US 8,440,203 B2
(45) Date of Patent: May 14, 2013

(54) METHODS OF IMMUNIZING PREGNANT HEIFERS AT THREE MONTHS OF GESTATION

(75) Inventors: Terri L. Wasmoen, Omaha, NE (US);
Huchappa Jayappa, Omaha, NE (US);
Randall Gene Davis, Elkhorn, NE (US);
Catherine M. Peters, Clare, IA (US)

(73) Assignee: Intervet Inc., Summit, NJ (US)

( * ) Notice: Subject to any disclaimer, the term of this patent is extended or adjusted under 35 U.S.C. 154(b) by 0 days.

(21) Appl. No.: 12/682,464

(22) PCT Filed: Nov. 6, 2009

(86) PCT No.: PCT/US2009/063467
§ 371 (c)(1),
(2), (4) Date: Mar. 3, 2011

(87) PCT Pub. No.: WO2011/056175
PCT Pub. Date: May 12, 2011

(65) Prior Publication Data
US 2011/0177116 A1  Jul. 21, 2011

(51) Int. Cl.
| | |
|---|---|
| A61K 39/215 | (2006.01) |
| A61K 39/00 | (2006.01) |
| A61K 39/295 | (2006.01) |
| A61K 35/20 | (2006.01) |
| A61K 39/40 | (2006.01) |
| A61K 39/08 | (2006.01) |
| A61K 39/15 | (2006.01) |
| A61K 39/108 | (2006.01) |

(52) U.S. Cl.
USPC ............... 424/221.1; 424/157.1; 424/184.1; 424/201.1; 424/202.1; 424/813; 424/823; 424/535; 424/167.1; 424/247.1; 424/215.1; 424/241.1; 424/257.1

(58) Field of Classification Search .............. None
See application file for complete search history.

(56) References Cited

U.S. PATENT DOCUMENTS

| | | | |
|---|---|---|---|
| 3,839,556 A | 10/1974 | Mebus et al. | |
| 3,869,547 A | 3/1975 | Mebus et al. | |
| 3,873,422 A | 3/1975 | Mebus | |
| 3,914,408 A | 10/1975 | Mebus | |
| 3,919,412 A | 11/1975 | Mebus | |
| 3,919,413 A | 11/1975 | Mebus | |
| 4,141,970 A | 2/1979 | Chidlow et al. | |
| 4,298,597 A | 11/1981 | Acres et al. | |
| 4,338,298 A | 7/1982 | Myers | |
| 7,309,493 B2 * | 12/2007 | Knape et al. | 424/201.1 |
| 2002/0086031 A1 * | 7/2002 | Audonnet et al. | 424/190.1 |
| 2005/0106163 A1 * | 5/2005 | David et al. | 424/190.1 |
| 2006/0286109 A1 * | 12/2006 | Audonnet et al. | 424/151.1 |
| 2009/0068223 A1 * | 3/2009 | Meyers et al. | 424/201.1 |
| 2010/0178301 A1 * | 7/2010 | Rinehart et al. | 424/201.1 |
| 2010/0272759 A1 * | 10/2010 | Beck et al. | 424/264.1 |

FOREIGN PATENT DOCUMENTS

| | | |
|---|---|---|
| EP | 0 028 172 B1 | 10/1979 |
| JP | 1994247878 A | 9/1994 |
| JP | 1998203998 A | 8/1998 |
| RU | 2145236 C1 | 2/2000 |
| RU | 2264458 C1 | 11/2005 |
| RU | 2275935 C1 | 5/2006 |
| RU | 2295975 C1 | 3/2007 |
| RU | 2301060 C1 | 6/2007 |
| RU | 2301079 C2 | 6/2007 |
| RU | 2320350 C1 | 3/2008 |
| RU | 2333748 C1 | 9/2008 |
| RU | 2366458 C1 | 9/2009 |
| RU | 2378017 C2 | 1/2010 |
| RU | 2403063 C1 | 11/2010 |
| RU | 2428202 C1 | 9/2011 |
| WO | 96/41874 A1 | 12/1996 |
| WO | 98/40097 A2 | 9/1998 |
| WO | 01/45735 A2 | 6/2001 |
| WO | 02/062382 A1 | 8/2002 |
| WO | WO 02/062382 A1 * | 8/2002 |
| WO | 2005/016383 A1 | 2/2005 |
| WO | 2008/118691 A2 | 10/2008 |
| WO | 2010/120195 A1 | 10/2010 |

OTHER PUBLICATIONS

Guardian article found at http:www.merck-animal-health-usa.com/130__163325/productdetails__130__163625.aspx dated Jan. 9, 2012.
Jayappa et al., "Demonstration of Passive Protection in Neonatal Calves against Colibacit osis Following Immunization of Pregnant Heifers at 3 Months of Gestation", Veterinary Therapeutics, Veterinary Learning Systenis. Sep. 1, 2006, pp. 283-298, vol. 9, No. 4.
International Search Report corresponding to PCT/US2009/063467 dated Mar. 10, 2010.
Aich et al., "Comparative analysis of innate immune responses following infection of newborn calves with bovine rotavirus and bovine coronavirus", Journal of General Virology, 2007, pp. 2749-2761, vol. 88.
Kohara et al., "Enhancement of Passive Immunity with Maternal Vaccine against Newborn Calf Diarrhea", Journal of Veterinary Medical Science, 1997, pp. 1023-1025, vol. 59, No. 1.
Troxel et al., "Clostridial vaccination efficacy on stimulating and maintaining as immune response in beef cows and calves", Journal of Animal Science, 1997, pp. 19-25, vol. 75.

* cited by examiner

Primary Examiner — Vanessa L Ford
Assistant Examiner — Lakia Tongue

(57) ABSTRACT

The present invention discloses methods for protecting newborn calves against neonatal diarrhea by vaccinating pregnant cows and/or pregnant heifers, while minimizing the number of separate occasions producers are required to assemble the cattle.

24 Claims, No Drawings

METHODS OF IMMUNIZING PREGNANT HEIFERS AT THREE MONTHS OF GESTATION

TECHNICAL FIELD

The present invention relates to veterinary vaccines generally, and more particularly to the vaccination of pregnant heifers and/or pregnant cows to provide immune protection to new born calves.

BACKGROUND

Neonatal diarrhea in calves, also known as scours, causes significant economic loss to the cattle industry. There are several etiological agents that are associated with neonatal diarrhea. The most common ones are rotavirus, coronavirus, *cryptosporidium, clostridium perfringens* [type(s) A, B, C, and/or D] and *E. coli*. A current method of combating these pathogens in neonates is through passive protection via maternal vaccination. Accordingly, vaccines are administered to pregnant cattle to provide passive protection to neonatal calves through ingestion of colostrum. Typically, such vaccines are administered to the pregnant animals 2-3 months prior to calving. For example, a common vaccine made up of Bovine Rotavirus-Coronavirus Vaccine, Killed Virus, *C. perfringens* Type C&D-*Escherichia coli* Bacterin-Toxoid has a product label that recommends two doses (2 mL/dose) administered subcutaneously to healthy, pregnant heifers and/or pregnant cows, with the primary vaccination three months prior to parturition and a booster 3-6 weeks following the initial administration. For subsequent annual vaccinations, the current label recommends revaccinating with a single 2 mL dose 5-7 weeks prior to calving.

Whereas it has long been a common practice for producers to check their cattle for pregnancy at approximately 3 months gestation, i.e., at approximately 6 months prior to calving, heretofore vaccines have been initially administered to cattle 2 to 3 months prior to calving and as a booster approximately 1 to 2 months prior to calving. This procedure requires producers to assemble individual cattle on multiple separate occasions, which results in increased stress on the animals and increased costs for the producers. Therefore, there is a need to develop new procedures that lower the number of times producers are required to assemble individual heifers and/or cows.

The citation of any reference herein should not be construed as an admission that such reference is available as "prior art" to the instant application.

BRIEF SUMMARY OF THE INVENTION

The present invention provides methods that can be used to protect against neonatal diarrhea (also known as scours). Methods provided by the present invention also can be used as an aid in the prevention of neonatal calf diarrhea. The present invention further provides methods that can be used in the control of neonatal calf diarrhea. Methods provided by the present invention also can be used to provide passive immunity against neonatal calf diarrhea. In addition, the present invention provides methods for protecting against neonatal diarrhea and/or aiding in the prevention of neonatal diarrhea, and/or providing passive immunity against neonatal calf diarrhea while also reducing the number of separate occasions a producer is required to assemble the cattle.

Accordingly, methods of the present invention can comprise administering to a pregnant bovine, i.e., a pregnant heifer or pregnant cow, an effective immunizing amount of a vaccine comprising an antigen from a pathogen associated with neonatal diarrhea (e.g., a primary vaccine) at about 5 to 7 months prior to parturition (at about 2 to 4 months post-conception). After parturition the calf is provided colostrum from one or more such vaccinated heifers and/or vaccinated cows. The calf receives passive immunity through ingestion of colostrum. In particular embodiments, the vaccine, e.g., a primary vaccine, is administered about 5 to 6 months prior to parturition (at about 3 to 4 months post-conception). In related embodiments the vaccine, e.g., a primary vaccine, is administered about 6 months prior to parturition, at about 3 months post-conception.

The colostrum may be provided directly, i.e., by allowing the calf to nurse directly from a vaccinated cow and/or a vaccinated heifer, or indirectly, e.g., by bottle feeding the calf colostrum obtained from one or more such vaccinated heifers and/or vaccinated cows. In certain embodiments, after a vaccinated pregnant heifer or a vaccinated pregnant cow gives birth to a calf, the calf is allowed to nurse from that vaccinated heifer or vaccinated cow. In certain embodiments, after a vaccinated pregnant heifer or a vaccinated pregnant cow gives birth to a calf, the calf is bottle-fed with colostrum obtained from that vaccinated heifer or vaccinated cow.

A pathogen associated with neonatal diarrhea can be any pathogenic agent that can cause neonatal diarrhea (i.e., an etiological agent) and/or one that leads to an increase in the severity of the disease. A pathogenic agent can be a bacterium, a virus, a protozoan, or any combination of these three pathogenic agents.

Any of the methods of the present invention can further comprise administering a booster vaccine 2 to 6 weeks after the administering of the primary vaccine. In particular embodiments the booster vaccine is administered 3 to 6 weeks after the administering of the primary vaccine. In more particular embodiments the booster vaccine is administered 4 weeks following initial vaccination. In most embodiments the booster vaccine will be identical to that of the primary vaccine. In other embodiments, the booster vaccine will be missing one or more components of the primary vaccine. In still other embodiments the booster vaccine will contain one or more components not in the primary vaccine. In yet other embodiments the booster vaccine will have components that have been substituted for those in the primary vaccine.

In certain embodiments the vaccine comprises inactivated *Escherichia coli* (*E. coli*) or an extract thereof. In particular embodiments of this type, the extract is a cell-free extract of *E. coli* pilus type K99. In other embodiments the extract is a cell-free extract of *E. coli* pilus type F41. In still other embodiments the extract is a combination of cell-free extracts of *E. coli* pilus type K99 and *E. coli* pilus type F41. In yet other embodiments the vaccine comprises one or more (e.g., 2) inactivated bovine corona virus strains. In still other embodiments the vaccine comprises one or more inactivated (e.g., 2) bovine rotavirus strains. In yet other embodiments the vaccine comprises a bacterin toxoid from *C. perfringens*. In particular embodiments of this type the bacterin toxoid is from *C. perfringens* type(s) A, and/or B, and/or C, and/or D. In still other embodiments the vaccine comprises an antigen from *cryptosporidium parvum*. In yet other embodiments of the present invention, the vaccine comprises combinations of all or any of the pathogens listed above. Thus in some embodiments the vaccine comprises a cell-free extract of *E. coli* pilus type K99 and/or *E. coli* pilus type F41, two (or more) inactivated bovine coronavirus strains, a *C. perfringens* bacterin toxoid from *C. perfringens* type(s) A, and/or B, and/or C, and/or D, two (or more) inactivated rotavirus strains, and/or an antigen from *cryptosporidium parvum*. In particular embodiments the vaccine comprises a cell-free extract of K99 pilus type of *E.coli*, a combination of two inactivated coronaviruses strains, two G-types of inactivated rotavirus strains, and a bacterin toxoid from *C. perfringens* types C and D. In one such vaccine of this type, the vaccine is a multiple antigen product GUARDIAN® Scours Vaccine, which contains a cell-free extract of K99 pilus type of *E. coli*, a combination of two inactivated coronaviruses strains, two G-types of inactivated rotavirus strains, and a bacterin toxoid from *C. perfringens* types C and D and is marketed by Intervet/Schering-Plough Animal Health.

In a related aspect, the present invention provides methods for providing passive immunity and/or protection against enterotoxemia. Such methods can comprise administering to a heifer or cow that is pregnant with a calf an effective immunizing amount of a vaccine (e.g., a primary vaccine) at about 5 to 7 months prior to parturition in which the vaccine comprises a bacterin toxoid from *C. perfringens*. Such embodiments comprise administering a vaccine that comprises a bacterin toxoid from *C. perfringens* types C and/or D (and/or *C. perfringens* types A and/or B) to a pregnant heifer or a pregnant cow at about 5 to 7 months prior to parturition. After parturition the calf is provided colostrum from one or more such vaccinated heifers and/or vaccinated cows. The calf receives passive immunity and/or protection from ingestion of colostrum against enterotoxemia that is due to *C. perfringens*. In particular embodiments, the vaccine, e.g., a primary vaccine, is administered about 5 to 6 months prior to parturition. In related embodiments the vaccine, e.g., a primary vaccine, is administered about 6 months prior to parturition. Such methods also can further comprise administering a booster dose of the vaccine 2 to 6 weeks after the administering of the primary vaccine. In particular embodiments the booster vaccine is administered 3 to 6 weeks after the administering of the primary vaccine.

In still another related aspect of the present invention methods are provided for aiding in the protection of calves from neonatal diarrhea by vaccinating pregnant cows and/or pregnant heifers, while minimizing and/or reducing the number of separate occasions producers are required to the pregnant cows and/or pregnant heifers. In certain such embodiments the method comprises administering to a heifer or cow that is pregnant with a calf an effective immunizing amount of a primary vaccine on the same occasion that the heifer or cow is checked for pregnancy. After parturition the calf is provided colostrum from one or more such vaccinated heifers and/or vaccinated cows. In this manner the number of separate occasions a producer is required to assemble the cattle is reduced and the calf receives protection from neonatal diarrhea e.g., from maternal antibodies and/or ingestion of colostrums.

The present invention therefore, provides methods for aiding in the prevention of neonatal diarrhea. Some such embodiments comprise administering to a pregnant heifer or pregnant cow at about 5 to 7 months prior to parturition a vaccine that comprises an antigen from a pathogen associated with and/or that causes neonatal diarrhea. After parturition the calf is provided colostrum from one or more of such vaccinated heifers and/or vaccinated cows. In certain embodiments, after the pregnant heifer or pregnant cow gives birth to a calf, the calf is then allowed to nurse from that heifer or cow. In certain embodiments, after a vaccinated pregnant heifer or a vaccinated pregnant cow gives birth to a calf, the calf is bottle-fed with colostrum obtained from that vaccinated heifer or vaccinated cow.

The present invention also provides methods for aiding in the control of neonatal diarrhea. Certain such embodiments comprise administering a vaccine, e.g., a primary vaccine, that comprises one or more (e.g., 2) inactivated bovine coronavirus strains to a pregnant heifer or a pregnant cow at about 5 to 7 months prior to parturition. In particular embodiments, the vaccine, e.g., a primary vaccine, is administered about 5 to 6 months prior to parturition. In related embodiments the vaccine, e.g., a primary vaccine, is administered about 6 months prior to parturition. After parturition the calf is provided colostrum from one or more such vaccinated heifers and/or vaccinated cows. In certain such embodiments, after the pregnant heifer or pregnant cow gives birth to a calf, the calf is then allowed to nurse from that heifer or cow. In certain embodiments, after a vaccinated pregnant heifer or a vaccinated pregnant cow gives birth to a calf, the calf is bottle-fed with colostrum obtained from that vaccinated heifer or vaccinated cow.

The vaccines of the present invention may contain an adjuvant. Such adjuvants include but are not limited to surface active substances like polymers or block-polymers including carbopol, DEAE dextran, saponins and their derivatives, detergents such as tween-80, pluronics, emulsions of mineral or vegetable oil or animal oils (squalane/squalene), aluminum salts (aluminum hydroxide and aluminum phosphate). The adjuvant combination may be presented in aqueous, oil, encapsulated (control or delayed release) or microencapsulated forms.

These and other aspects of the present invention will be better appreciated by reference to the following Detailed Description.

DETAILED DESCRIPTION OF THE INVENTION

In one aspect, the present invention provides new procedures that lower the number of separate occasions producers are required to assemble individual cattle. In particular embodiments the number of times that an individual heifer and/or cow is individually assembled is reduced by administering a vaccine containing Rotavirus, and/or Coronavirus, and/or *Clostridium perfringens* (alpha and/or, beta and/or epsilon toxoid), and/or *Escherichia coli* (K99 and/or F41 fimbriae), and/or an antigen from *cryptosporidium* at the same time as the heifer and/or cow is checked for pregnancy. In related embodiments, such a vaccine is administered to pregnant heifers and/or pregnant cows at 2 to 4 months gestation, i.e., at 5 to 7 months prior to calving to provide passive immunity to neonatal calves. In particular embodiments such a vaccine is administered to pregnant heifers and/or pregnant cows at about 3 months gestation, (i.e., at about 6 months prior to calving) to provide passive immunity to neonatal calves.

All of the methodology provided herein is appropriate for the dairy industry, in which newborn calves are manually fed with a bottle containing the colostrum, and/or for the beef industry, in which the calves are allowed to nurse directly from the cow or heifer. Thus, the new born (e.g., day old) calf is provided colostrum from the vaccinated cows or heifers either directly through nursing, or indirectly, e.g., through bottle feeding with colostrum from vaccinated cattle.

Accordingly, the present invention relates to a method of vaccinating pregnant cattle (heifers or cows) 5 to 7 months prior to calving [see e.g., Jayappa et al., *Veterinary Therapeutics* 9(4) 283-289 (2008), the contents of which are hereby incorporated in their entireties by reference]. The vaccine can be as a monovalent vaccine or in any combination vaccine comprising Rotavirus, Coronavirus, *Clostridium perfringens* (alpha, beta and epsilon toxoid), *Escherichia coli* (K99 and/or F41 fimbirae), and/or an antigen from *cryptosporidium par-*

*vum*. The vaccine may be given as single dose or in two or more doses, with the first dose coinciding with checking the heifer and/or cow for pregnancy.

In another aspect, the present invention provides new procedures for providing passive immunity to a day old calf against *C. perfringens*. One such method comprises administering to a pregnant heifer and/or pregnant cow an effective immunizing amount of a vaccine composition against *C. perfringens* at 5 to 7 months prior to parturition of the calf, i.e., at 2 to 4 months gestation of the calf. In particular embodiments, the methods comprise administering to the pregnant heifer and/or pregnant cow an effective immunizing amount of a vaccine composition against *C. perfringens* at about 6 months prior to parturition of the calf, i.e., at about 3 months gestation.

In certain embodiments the vaccine against *C. perfringens* comprises antigens that elicit an immune response to *C. perfringens* types A and/or B and/or C and/or D. In certain embodiments, the vaccine against *C. perfringens* may elicit an antibody response to *C. perfringens* type A alpha toxoid and/or *C. perfringens* type C beta toxoid and/or *C. perfringens* type D epsilon toxoid in the pregnant heifer and/or pregnant cow and/or in the calf.

In particular embodiments, the colostrum from the cow/heifer and/or the calf's serum (following ingestion of colostrum from the vaccinated cow/heifer soon after birth) may comprise antitoxin to *C. perfringens* alpha and/or beta and/or epsilon toxin. In certain embodiments, the colostrum from the cow/heifer and/or the calf's serum (following ingestion of colostrum from the vaccinated cow/heifer soon after birth) may comprise at least about 1 epsilon antitoxin unit/mL. In certain embodiments, the colostrum from the cow/heifer and/or the calf's serum (following ingestion of colostrum from the vaccinated cow/heifer soon after birth) may comprise about 2 beta antitoxin units/mL. In certain embodiments, the colostrum from the cow/heifer and/or the calf's serum (following ingestion of colostrum from the vaccinated cow/heifer soon after birth) may comprise about 1 alpha antitoxin unit/mL.

In particular embodiments, the antigen may be a *C. perfringens* bacterin. In additional embodiments, the antigen may be isolated or derived from *C. perfringens* bacteria that have been inactivated by any suitable method available to one of ordinary skill in the art. Examples of such inactivation methods include, but are not limited to, heat, formaldehyde, formalin, binary ethylenimine (BEI), radiation, and beta-propiolactone treatment. In particular embodiments, the *C. perfringens* bacteria may be inactivated by formalin treatment.

In certain embodiments, a method is provided for providing protection from and/or aid in the prevention of neonatal diarrhea due to *E. coli* to a day old calf. In particular embodiments the method comprises administering to a pregnant heifer and/or pregnant cow an effective immunizing amount of a vaccine composition against *E. coli* 5 to 7 months prior to parturition of the calf, i.e., at 2 to 4 months gestation. In particular embodiments, the method comprises administering to a pregnant heifer an effective immunizing amount of a vaccine composition against *E. coli* about 6 months prior to parturition of the calf, i.e., at about 3 months gestation.

In certain embodiments, the vaccine against *E. coli* may comprise antigens that elicit an immune response to *E. coli* K99 and/or F41 pilus. In particular embodiments, the vaccine against *E. coli* may elicit an antibody response to *E. coli* K99 and/or F41 pilus in the pregnant heifer and/or pregnant cow, and by passive transfer to the calf. In certain embodiments, the colostrum and the calf's serum (following ingestion of colostrum from the vaccinated cow/heifer soon after birth) may comprise antibodies to *E. coli* K99 pilus and/or F41 pilus. In particular embodiments the colostrum and the calf's serum (following ingestion of colostrum from the vaccinated cow/heifer after birth) may comprise an antibody titer to K99 antigen of more than about 8.

In certain embodiments, the antigen may be an *E. coli* bacterin. In additional embodiments, the antigen may be isolated or derived from *E. coli* that have been inactivated by any suitable method available to one of ordinary skill in the art. Examples of such methods include, but are not limited to, heat, formaldehyde, formalin, binary ethylenimine, radiation, and beta-propiolactone treatment. In particular embodiments, the *E. coli* may be inactivated by formalin treatment.

In particular embodiments, a method is provided for providing protection from and/or aid in the prevention of neonatal diarrhea due to Bovine coronavirus (BCV) to a day old calf, the method comprising administering to a heifer and/or cow pregnant with the calf an effective immunizing amount of a vaccine composition against BCV 5 to 7 months prior to parturition of the calf, i.e., at 2 to 4 months gestation. In particular embodiments, the method comprises administering to a pregnant heifer and/or pregnant cow an effective immunizing amount of a vaccine composition against BCV about 6 months prior to parturition of the calf, i.e., at about 3 months gestation. In certain embodiments, the vaccine against BCV may comprise antigens that elicit an immune response to BCV. In certain embodiments, the vaccine against BCV may elicit an antibody response to BCV in the pregnant heifer and/or pregnant cow and/or in the calf following ingestion of colostrum from the vaccinated dam. In certain embodiments, the colostrum of the heifer and/or cow may comprise antibodies to BCV.

In certain embodiments, the antigen may be an attenuated, inactivated, or killed BCV. For example, the BCV can be bovine coronavirus type 1 and/or type 3. Multiple strains of BCV can be included, such as a combination of BCV type 1 and type 3 either alone or together with other BCV types, combinations of type 1 or type 3 with other BCV types, and combinations of BCV types that do not include either BCV type 1 and type 3. In certain embodiments, the antigen may be isolated or derived from BCV that have been inactivated or killed by any suitable method available to one of ordinary skill in the art. Examples of such methods include, but are not limited to, heat, formaldehyde, formalin, binary ethylenimine, radiation, and beta-propiolactone treatment.

In certain embodiments, the antigen may be an attenuated, inactivated, or killed rotavirus. Exemplary rotavirus strains include strain G10, and strain G6. Multiple strains of rotavirus can be included, such as a combination of rotavirus strains G10 and G6 either alone or together with other rotavirus strains such as strain G8, combinations of G10 or G6 or G8 with other rotavirus strains, and combinations of rotavirus strains that do not include rotavirus strains G8 or G10 or G6. In certain embodiments, the rotavirus antigen may be isolated or derived from rotavirus that have been inactivated or killed by any suitable method available to one of ordinary skill in the art. Examples of such methods include, but are not limited to, heat, formaldehyde, formalin, binary ethylenimine, radiation, and beta-propiolactone treatment.

In certain embodiments, one or more cryptosporidium antigens may be included in the vaccine. Such antigens can be, for example, cryptosporidium proteins. In certain embodiments the cryptosporidium proteins are recombinant proteins. Recombinant cryptosporidium proteins can be readily expressed by methodology well known in the art, e.g., an *E. coli* expression system, a baculovirus expression system, or a recombinant mammalian or avian recombinant virus, such as a recombinant bovine adenovirus. Examples of cryptosporidium proteins that may be used as antigens include Cp15/60, Cp23, and P21.

Accordingly, the present invention provides methods for use in healthy cows and heifers that aid in the prevention of neonatal calf diarrhea caused by enterotoxigenic *E. coli* pilus type 99 and/or *E. coli* pilus type 41, bovine Group A serotype G6 and G10 rotaviruses; enterotoxemia caused by *C. perfringens* Type C and D strains; and as an aid in the control of neonatal calf diarrhea caused by bovine coronaviruses. Therefore, in certain embodiments, the vaccine composition may comprise one or more other active components such as, but not limited to, an antipathogenic component directed against, or an antigenic component of, *E. coli, E. coli* bacterin toxoid, *E. coli* K99 and/or F41 pili, bovine rotavirus (e.g., rotavirus strains G10 and/or G6 and/or G8), bovine coronavirous (e.g., coronavirus strains type 1 and/or type 3) and/or cryptosporidium.

In certain embodiments, the vaccine composition may include one or more pharmaceutically acceptable adjuvants. Examples of pharmaceutically acceptable adjuvants are well known in the art, see, e.g. REMINGTON'S PHARMACEUTICAL SCIENCES, 18th Ed. [Mack Publishing Co., Easton, Pa. (1990)] and GOODMAN AND GILMAN'S, THE PHARMACOLOGICAL BASIS OF THERAPEUTICS ($10^{th}$ ed. 2001). In certain embodiments, the adjuvant can stimulate a cell-mediated immune response. In other embodiments, the adjuvant can stimulate a humoral immune response. In still other embodiments the adjuvant can stimulate both a cell-mediated immune response and a humoral immune response.

In certain embodiments, the vaccine composition may comprise one or more pharmaceutically or veterinarily acceptable carrier or diluents. Non-limiting examples of carriers or diluents that may be used in vaccine composition formulations include HEPES buffer, Fisher's media, water, saline, phosphate buffered saline, Hank's solution, Ringer's solutions, dextrose/saline, glucose solutions, etc. The formulations may contain pharmaceutically acceptable auxiliary substances to enhance stability, deliverability or solubility, such as buffering agents, tonicity adjusting agents, wetting agents, detergents and the like. Additives may also include additional active ingredients such as bactericidal agents or stabilizers. For example, the solution may contain thimerosal, gentamycin, sodium acetate, sodium lactate, sodium chloride, potassium chloride, calcium chloride, sorbitan mono-laurate, and/or triethanolamine oleate. Compositions may be sterilized by conventional, known sterilization techniques.

In certain embodiments, the vaccine composition may be formulated in a dosage unit form to facilitate administration and ensure uniformity of dosage. Herein, a "dosage unit" as it pertains to the vaccine composition refers to physically discrete units suitable as unitary dosages for a subject, each unit containing a predetermined quantity of e.g., *C. perfringens, E. coli*, bovine rotavirus, bovine coronavirus and/or cryptosporidium antigen calculated to produce the desired immunogenic effect in association with an adjuvant, carrier, and/or vehicle.

In certain embodiments the vaccine composition may be administered parenterally, for example, intramuscularly, subcutaneously, intraperitoneally, intradermally or the like.

Accordingly, embodiments of the invention also provide methods for the prevention and/or amelioration of *C. perfringens, E. coli*, bovine rotavirus, bovine coronavirus and/or cryptosporidium infection in a calf that comprises administering to a heifer and/or cow pregnant with the calf a vaccine composition of the present invention at least about 6 months prior to parturition, i.e., at about 3 months gestation In certain embodiments, the vaccine composition of the invention may be administered, e.g., parenterally, in effective amounts according to a schedule determined by the time of potential exposure to *C. perfringens, E. coli*, bovine rotavirus, bovine coronavirus and/or cryptosporidium. In this way, the treated heifer and/or treated cow may have time to build immunity prior to parturition and transfer of passive immunity to the calf. For example, one treatment schedule of the present invention may include subcutaneous injection at least 5 months prior to parturition, i.e., at about 4 months gestation. A more typical treatment schedule for the present invention may include subcutaneous injection at least 6 months prior to parturition, i.e., at about 3 months gestation. In certain embodiments, more than one administration of the vaccine composition may be provided to a heifer and/or cow pregnant with a calf. By way of non-limiting example, a first administration is made at about 6 months prior to parturition or at about 3 months gestation of a calf, and a second at about 4 weeks after the first administration, i.e., at about 5 months prior to parturition or at about 4 months gestation of the calf. In particular embodiments, the second administration of the vaccine is at 3 to 5 weeks following the first administration. In certain embodiments, subsequent annual vaccinations, involves revaccination of a pregnant heifer and/or cow 5 to 7 weeks prior to calving. In other embodiments, subsequent annual vaccinations, involves revaccination of a pregnant heifer and/or pregnant cow 5 to 7 months prior to calving. In certain embodiments the vaccination and subsequent annual revaccination is with a single 2 mL dose of vaccine.

As used herein the following terms will have the following meaning:

As used herein "about 6 months prior to parturition" means between 5½ months to 6½ months prior to parturition; "about 5 months prior to parturition" means between 4½ months to 5½ months prior to parturition; "about 5 to 6 months prior to parturition" means between 4½ months to 6½ months prior to parturition; and "about 5 to 7 months prior to parturition" means between 4½ months to 7½ months prior to parturition.

As used herein "prior to parturition" is equivalent to "prior to calving".

As used herein, "about 3 months gestation" means between 2½ and 3½ months gestation.

As used herein, "about 4 weeks" means between 2 to 6 weeks.

An "effective immunizing amount," as used herein, may vary depending upon the strain or strains of *C. perfringens, E. coli*, bovine rotavirus, bovine coronavirus and/or cryptosporidium used to generate the vaccine and is an amount that is sufficient (and/or more than sufficient) to evoke a protective immune response to the corresponding pathogen in the pregnant heifer and/or the pregnant cow and/or transfer of protective passive immunity to the new-born calf.

"Protecting" or "providing protection to" does not require complete protection from any indication of infection. Rather, it means that protection is sufficient such that, after challenge, symptoms of the underlying infection are at least reduced, and/or that one or more of the underlying cellular, physiological, or biochemical causes or mechanisms causing the symptoms are reduced and/or eliminated. It is understood that "reduced," as used in this context, means relative to the state of the infection, including the molecular state of the infection, not just the physiological state of the infection.

The following illustrative examples are provided to further describe the invention.

EXAMPLE 1

Evaluation of 6 Months Duration of Immunity for Clostridial Fractions of a Bovine Rotavirus-Coronavirus Vaccine, Killed Virus, C. perfringens Type C&D, E. coli Bacterin-Toxoid Introduction:

Enterotoxigenic *E. coli*, bovine coronavirus, bovine rotavirus and *C. perfringens* Type C and D strains have been reported to be a major cause of neonatal calf diarrhea. Calves less than one to two weeks old are highly susceptible to the diseases caused by these organisms. Current product labels for multivalent vaccines that comprise bovine Rotavirus-Coronavirus, Killed Virus, *C. perfringens* Type C&D and *E. coli* Bacterin-Toxoid recommend two doses (2 mL/dose) administered subcutaneously to healthy, pregnant heifers/cows, with the primary vaccination three months prior to parturition and a booster 3-6 weeks following the initial administration. For subsequent annual vaccinations, the current label recommends revaccinating with a single 2 mL dose 5-7 weeks prior to calving. This study demonstrates a protective titer to *C. perfringens* Type C&D by vaccination at six months prior to partuition with a Bovine Rotavirus, Coronavirus, *C. perfringens* Type C&D, and *E. coli* bacterin toxoid.

Study Protocol

Vaccine: Rotavirus, Coronavirus, *E. coli*, and *C. perfringens* Type C and D

Rotavirus, Coronavirus, *E. coli* antigens and *C. perfringens* Type C and D antigens were produced according to standard procedures in the art. Rotavirus and Coronavirus were inactivated with BEI. *Clostridium perfringens* Type C, Type D and *E. coli* were inactivated with formalin. Adjuvanting and Blending were performed according to standard procedures in the art. Sterility, safety and potency testing was conducted. Normal saline was used as the placebo.

Animals: Pregnant heifers at approximately 3 months gestation (approximately 6 months prior to parturition) with an initial age of greater than or equal to 13 months of age were vaccinated. The calves were newborns. The animals tested were cross-bred beef cattle (31 pregnant heifers and 31 bull or heifer calves). Pregnant heifers and their calves were identified using unique double ear tags.

Inclusion Criteria/Exclusion Criteria: Healthy heifers that were pregnant and at approximately 3 months gestation were included in the study if they had a low antibody titer for the *C. perfringens* beta and epsilon toxins, and the *E. coli* pilus antigen. One heifer in the vaccinated group was later found to be open and excluded from the study. One calf in the control group was weak and unable to stand after birth. Samples from the corresponding heifer were not tested.

Housing and Animal Husbandry: Animals were subjected to normal good husbandry practices throughout the study. Routine procedures were standardized across all animals. Heifers were housed on a pasture and did not come in direct contact with any other animals at the farm. The heifers in the two groups were comingled. Animals were supplied with water ad libitum throughout the study. The heifers were fed diets that met NRC nutrient requirements for cattle at their current production phase. No concurrent/concomitant medications or therapies were given.

Experimental Procedures:

Pre-Vaccination Monitoring: A blood sample was collected from all heifers prior to vaccination on day 0 to determine antitoxin titer to beta and epsilon toxin. All heifers were given a physical examination prior to vaccination on study day 0.

Administration of the Vaccine: Heifers at approximately 3 months gestation (e.g., 6 months before parturition) were vaccinated with 2 mL of the vaccine or placebo as previously described. The heifers were vaccinated by subcutaneous route in the mid-portion of the neck. A similar booster dose was administered 4 weeks following initial vaccination.

Post-Vaccination procedures: A blood sample was collected from all heifers just prior to or immediately after calving. Blood samples were collected from calves on the second day after birth following ingestion of colostrums. Colostrum was collected from each heifer immediately after calving. Colostrum samples were obtained from each heifer by milking an approximately equal volume of secretions from each quarter into one tube. Samples were frozen at -1020 C. or colder until processed.

Analytical Methods: Antitoxin Titer in Serum and Colostrum: Toxin neutralization titers (Antitoxin Units) in sera and colostrum were evaluated according to the 9 CFR regulations excepting that the test was conducted using cattle sera and/or colostrum.

Data Analysis:

Outcome Variables: The Primary Variable was the colostrum antitoxin titer to *C. perfringens* type C beta toxin and *C. Perfringens* type D epsilon toxin and the antitoxin titer in serum of day old calves. The Secondary Variable was the antitoxin titer in sera of heifers. The experimental unit was the pooled and individual colostrum from heifers and pooled sera from calves. The number of replicates per Treatment was 21 heifers and 21 calves born to vaccinated heifers; 10 heifers and 10 calves born to control heifers.

Test Validity and Acceptability Criteria: The study was valid as placebo control heifers showed no increase in antitoxin titer indicating that there was no natural exposure to infection. Importantly, antitoxin titer in the colostrum pool met the levels accepted as protective.

Results and Discussion

Heifers Gestation: Calving dates ranged from 154-205 days after first vaccination. The first dose of vaccine was administered 5 to 6 months prior to calving.

Immune Response to Clostridial Fractions:

Antitoxin Titer to *C. perfringens* type C beta toxin: Heifers serum and colostrum: The assay was first conducted using pooled samples. The pools were prepared by adding equal amounts of individual sample from each animal in the treatment group. The antitoxin titers to beta toxin for both vaccinate and control groups are shown in Table 1. The antitoxin titer in sera of control heifers at the time of vaccination was <1 AU and the titer remained unchanged at the conclusion of the study. These results confirm that there was no exposure to natural infection. The pooled sera from the vaccinate group had a titer of <1 AU at the time of vaccination and 1-5 AU at the time of calving. Typically, the antibody titer in the serum of heifers drops as the heifer approaches calving time due to migration of lymphocytes to mammary gland. The colostrum pool from vaccinated heifers had a titer of 20-25 AU. The results indicate that the colostrum titer is above the accepted level for protection (>10 AU). Individual colostrums samples from only the vaccinate group were then tested: with 71.4% (15/21) of the vaccinated heifers having a colostrums titer of ≧10; while 28.6% (6/21) of the vaccinated heifers had a colostrum titer of ≧5.

Antitoxin Titer to *C. perfringens* type C beta toxin: Serum Titer in Calves: The antibody titer in sera of calves born to control and vaccinated heifers are shown in Table 2. The sera from the control group had a titer of <1 AU and the sera from the vaccinated group had a titer of 5-10 AU.

Antitoxin Titer to *C. perfringens* type D epsilon Toxin: Heifers serum and colostrum: The antitoxin titers to epsilon toxin for both vaccinate and control group are shown in Table 3. The antitoxin titer in sera of control heifers at the time of vaccination was <1 AU and the titer remained unchanged at the conclusion of the study. These results confirm that there was no exposure to natural infection. The pooled sera from the vaccinate group had a titer of <1 AU at the time of vaccination and 1-2 AU at the time of calving. The colostrum pool from vaccinated heifers had a titer of >2 AU. The results indicate that the colostrum titer is above the accepted level for protection ($\geq 2$ AU). Individual colostrum samples from only the vaccinate group were then tested, with 71.4% (15/21) of the vaccinated heifers having a colostrums titer of $\geq 2$.

Antitoxin Titer to *C. perfringens* type D epsilon Toxin: Serum Titer in Calves: The antibody titer in sera of calves born to control and vaccinated heifers are shown in Table 4. The sera from control group had a titer of <1 AU and the sera from vaccinated group had a titer of 1-2 AU.

Conclusions:

The serum pool from control heifers showed no change in antibody titer throughout the study suggesting that there was no exposure to natural infection. The sera from vaccinated heifers collected at the time of calving had an antitoxin titer to both beta and epsilon toxin. The colostrums from vaccinated heifers had an antitoxin titer to both beta and epsilon toxin at a higher level than is considered to be protective. The calves born to the vaccinated heifers had an antitoxin titer in their sera confirming the transfer of passive antibodies. The data demonstrate that the heifers can be vaccinated as early as 6 months prior to calving and still show a satisfactory level of antitoxin titer in the colostrum for passive transfer.

EXAMPLE 2

Efficacy of the *E. coli* K99 Fraction of a Bovine Rotavirus-Coronavirus Vaccine *C. perfringens* Type C&D-*E. coli* Bacterin-Toxoid Administered Six Months Prior to Parturition Introduction:

Enterotoxigenic *E. coli*, bovine coronavirus, bovine rotavirus and *C. perfringens* Type C and D strains have been reported to be a major cause of neonatal calf diarrhea. Calves less than one to two weeks old are highly susceptible to the diseases caused by these organisms. The current product label for a bovine Rotavirus-Coronavirus Vaccine-*C. perfringens* Type C&D-*E. coli* Bacterin-Toxoid vaccine recommends two doses (2 mL/dose) administered subcutaneously to healthy, pregnant heifers/pregnant cows, with the primary vaccination three months prior to parturition and a booster 3-6 weeks following the initial administration. For subsequent annual vaccinations, the current label recommends revaccinating with a single 2 mL dose 5-7 weeks prior to calving. This study demonstrates the efficacy of the *E. coli* fraction of a Bovine Rotavirus, Coronavirus, *C. perfringens* Type C&D, and *E. coli* bacterin toxoid with an initial vaccination at six months prior to parturition.

Study Design and Experimental Procedures:

The present study was conducted concurrently with the study presented in Example 1 with the same animals. All vaccination procedures and samplings are detailed in Example 1. Further actions, tests, and data collected beyond Example 1 are presented below.

Pre-Challenge Procedures: Each calf was allowed to nurse prior to the challenge with virulent *E. coli*.

Challenge: A heterologous *E. coli* challenge culture was used to challenge all calves. The calf was returned to the cow immediately following the challenge.

Post-Challenge Monitoring: For ten days following the challenge the calves were observed for clinical signs including incidence of scours, severity of scours, degree of dehydration/depression and death.

Blood Samples: A blood sample was collected from each calf on day 1 after ingestion of colostrum to determine antibody titer to *E. coli* K99 pili.

Fecal samples: Samples of feces were collected from calves on days 0 through 5 following challenge and frozen at −10° C. or colder until assayed for isolation of *E. coli*.

Necropsy/Disposition: Post-Challenge Necropsy Observations & Specimens: A postmortem examination was performed on all calves that died following *E. coli* challenge to determine the cause of death.

Analytical Methods:

Serum Antibody Titer to *E. coli* K99 pilus antigen: The antibody titer to *E. coli* K99 pilus antigen in serum and colostrum was determined according to procedures standard in the art, e.g., by a microagglutination test.

*E. coli* K99 isolation: Samples of feces were collected from calves following challenge and were tested for *E. coli* K99 according to standard procedures in the art. *E. coli* was isolated on selective agar plates and these colonies were tested for K99 expression by an agglutination test using specific antiserum.

Data Analysis:

Outcome Variables: Primary Variable: Mortality due to scours; Secondary Variable: Severity of scours, dehydration/depression, antibody titer in colostrum and sera. The Experimental Unit was each individual calf. The number of replicates per treatment: 21 calves born to vaccinated heifers and 10 calves born to control heifers.

Test Validity and Acceptability Criteria: Validity: The study was valid as placebo-control heifers showed no increase in antibody titer indicating that there was no natural exposure to infection. The test was valid as more than 60% percent of calves born to control heifers died following challenge. Acceptability: Calves born to control heifers showed significantly higher ($P \leq 0.05$) mortality, severity of scours and dehydration/depression.

Results and Discussion

Heifers Gestation: Gestation status of the heifers at the time of vaccination is shown in Example 1 above. The calving dates ranged from 154-205 days after first vaccination. The first dose of vaccine was administered 5 to 6 months prior to calving.

Efficacy for *E. coli* K99 fraction: Mortality: As shown in Table 6, 80% (8/10) of the calves born to control heifers died following challenge. A total of 14% (3/21) calves born to vaccinated heifers died following challenge. The mortality in the control group was significantly higher than the vaccinate group (p=0.0007). The prevented fraction estimate for mortality was 82.1%, 95% CI (47.2%, 96.2. %). Necropsy findings confirmed that all calves died due to severe dehydration as a result of severe scours.

Severity of Scours: Two of ten control calves were not scored for clinical signs of scours due to early mortality. Seventy-five percent (6/8) of the remaining controls showed signs of severe scours compared to 28.6% (6/21) of vaccinates. The vaccine and control group were significantly different for severe scours (p=0.0382). The preventive fraction estimate for severe scours was 61.9%, 95% CI (−2.2%, 86, 1%). The maximum daily score for scours was significantly higher in the controls compared to vaccinates (median=4 in the control group vs. median=2 in the vaccine group, P=0.0139).

Degree of Dehydration/Depression: Two of 10 control calves were not scored for dehydration/depression due to early mortality. Seventy-five percent (6/8) of remaining control calves showed signs of severe dehydration/depression compared to 5% (1/21) of vaccinates. The severity of dehydration/depression for control group was significantly higher (p=0.0004) compared to vaccinate group. The preventive fraction estimate for severe dehydration/depression was 93.5%, 95% CI (66.3%, 99.8). The maximum daily score for dehydration/depression was significantly higher in the controls compared to vaccinates (median=4 in the control group vs. median=0 in the vaccine group (p=0.0005).

K99 Antibody Titers in Heifer's Serum, Calf Serum and Colostrum: Group geometric mean antibody titers are shown in Table 6. The control heifers had a pre-vaccination geometric mean titer of 4 and the titer did not change at the time of calving (geometric mean=4). These results indicate that there was no environmental exposure to E. coli infection. The vaccinated heifers had a pre-vaccination serum geometric mean titer of 4 which increased to 51 at Day 101 and 27 at the time of calving. The colostrum from the vaccinated and control heifers had a geometric mean titer of 92 and 9, respectively. The post-vaccination antibody titer in the serum and colostrum of vaccinated heifers was significantly higher than the controls (p<0.0001).

K99 Antibody Titers in Calves: The sera from the control group had a geometric mean titer of 4 whereas the sera from the vaccinate group has a titer of 16. The antibody titer in the sera of the vaccinated group was significantly higher (p=0.0079) compared to the controls.

Isolation of E. coli From Fecal Samples: Fecal samples from 2 calves in the control group were not collected due to early mortality. E. coli was re-isolated from the feces of all remaining 8 calves in the control group. E. coli was re-isolated from 20 out of 21 calves in the vaccinate group.

Isolation of E. coli From Intestinal Scrapings of Dead Calves: E. coli positive for K99 were isolated from 75% (6/8) of intestinal scrapings of dead calves in the control group. E. coli positive for K99 were isolated from 67% (2/3) of dead calves from the vaccinate group. Data on mortality confirm that the E. coli K99 is the cause of death.

Conclusions:

Eighty percent of the calves born to control heifers died following the challenge with E. coli showing that the challenge was sufficiently virulent to judge the vaccine efficacy. The calves born to vaccinated heifers had statistically significantly lower mortality compared to calves born to control heifers. The calves born to control heifers had significantly higher scours and dehydration/depression scores than calves born to vaccinated heifers. The vaccinated heifers demonstrated significantly higher antibody titer to K99 pilus antigen in serum and colostrum compared to controls. The serum of calves born to vaccinated heifers demonstrated significantly higher antibody titer to K99 pilus antigen.

EXAMPLE 3

Demonstration of Immunity for Coronavirus Fractions of a Bovine Rotavirus-Coronavirus Vaccine-C. perfringens-E. coli Type C&D Bacterin Toxoid Vaccine when Administered to Heifers Approximately Six Months Prior to Parturition Introduction:

It is common practice for producers to pregnancy check cows at approximately 3 months gestation. Therefore, it would be advantageous to vaccinate at 3 months gestation as opposed to the current recommendation of 6 months gestation (3 months prior to parturition) in order to provide cost and labor benefits as well as result in less stress for the animals. Previous studies were conducted to establish the minimum colostrums antibody titer, which protects against BCV. The results of these studies demonstrated a good correlation between colostrum antibody titer and passive protection in neonatal calves. This study demonstrates colostrum titers above the minimum protective antibody level against BCV when pregnant heifers are vaccinated at 3 months gestation (6 months prior to parturition).

Study Protocol

Vaccine: Rotavirus, Coronavirus, E. coli and C. perfringens Type C and D. The antigen fractions were produced according to standard procedures in the art. Adjuvanting and blending were performed according to standard procedures in the art. Sterility, safety and potency testing were also conducted. The placebo used was phosphate buffered saline.

Study Design

The fifty Heifers in the study were estimated to be 20 to 36 months old at enrollment and pregnant for approximately 32-55 days, based on the preliminary examination. The breed was Holstein. The heifers had an initial Body Weight Range of 370-475 kg. The identification method employed was an ear tag.

Inclusion/Exclusion Criteria: Pregnant heifers, in good health, free of clinical signs of disease and with low antibody titers to BCV were included. One heifer from Group 2 was not pregnant and therefore, was excluded in the analysis.

Housing and Animal Husbandry: Heifers were acclimated to the test facility for at least 2 weeks prior to first vaccination. The heifers were pastured and housed in open barns with sufficient space for their size and condition. They were segregated from other cattle at the facility. Heifers were fed a ration that met or exceeded NRC requirements for their age and stage of gestation. Water was provided ad libitum.

Experimental Procedures

Pre-Vaccination Monitoring/Acclimation: Blood samples were collected prior to purchase of the heifers. Heifers were examined and palpated on study day 0 to confirm good health and pregnancy.

Vaccination: Heifers were vaccinated with the appropriate test product on days 0 and 34. All vaccinations were administered by subcutaneous injection in the side of the neck, 2 mL per dose. Twenty-five heifers were vaccinated with the test vaccine, whereas twenty-four were administered the placebo.

Post-Vaccination Procedures: Blood was collected from all animals on the day of first vaccination (study day 0), the day of the second vaccination (study day 34), four weeks after the second vaccination (study day 62), at approximately 6, 7 and 8 months gestation, as well as on the day of calving. Heifers were observed daily for general health from acclimation until they were close to calving. At approximately 2 weeks prior to parturition, based on expected calving date or clinical signs indicating parturition may be imminent (e.g., swollen udder, relaxed pelvic ligaments), the heifers were observed at least 3 times daily for health and onset of parturition.

Assistance was provided during parturition, as required. The calves were removed from the cows before they could suckle, and the udders were checked for mastitis. Heifers were milked within 2 hours of calving and again 10-12 hours after calving. All samples were stored frozen at −10° C. or colder until testing.

Analytical Methods:

BCV Colostrum and Serum Antibody Assay: Antibody titers to BCV in colostrum samples were evaluated by indirect immunofluorescence assay per standard procedures. Titers were calculated using the Spearman Karber method and reported as $FAID_{50}/mL$.

Data Analysis The primary variable is the colostrum antibody titer to BCV. The experimental unit is the individual heifer colostrum. The number of replicates per treatment were twenty-five vaccinates and twenty-four control heifers.

Test Validity and Acceptability Criteria: The study met the acceptability criteria for the BCV fraction as the sera and colostrum from vaccinated heifers showed significantly higher antibody titers compared to controls.

Results and Discussion:

Serum Antibody Titer to BCV Type 1: Serum neutralizing antibody titers to BCV were evaluated from sera collected prior to vaccination, on Day 0, at the time of booster vaccination (Day 34), Day 62, at approximately 6, 7, and 8 months gestation as well, as on the day of calving (see, Table 7).

The geometric mean titer (GMT) of the vaccinate group peaked at Day 62 (GMT 4360). Although the titers slightly declined at 6, 7, and 8 months post vaccination, they remained high as compared to the control group. The GMT for both the vaccinate and the control groups dropped at the time of calving, probably due to the migration of immunoglobulin to the mammary glands. Group geometric mean serum titers to BCV Type III are shown in Tables 8. The antibody response was similar to BCV Type I as the vaccinate group titers remained higher than the control group throughout all time points.

Colostrum Antibody Titer to BCV: Group geometric mean colostrum antibody titers for BCV-Type I are shown in Table 9. The GMT of BCV-Type I for vaccinates and controls were 7538 and 1039, respectively. Group geometric mean colostrum antibody titers for BCV-Type III are shown in Table 10. The GMT of BCV-Type III for vaccinates and controls were 6517 and 790, respectively.

Establishing Minimum Colostrum Antibody Units for Protection for BCV fraction. The minimum colostrum antibody titer needed to provide passive protection in neonatal calves for the coronavirus fraction was previously established. The percentage of heifers in the vaccinate and control groups which had BCV Type I colostrum protective antibody titers, above the minimum protective level was 72% and 21%, respectively (see, Table 9). The prevented fraction vaccine efficacy was 64.6% (95% confidence interval 31.4%, 85.0%).

Conclusions:

Seventy two percent (72%) of the heifers in the vaccinate group demonstrated colostral antibody titers at or above the protective level six months following vaccination. The preventative fraction for efficacy was 64.6%. Only 21% of the heifers in the control group, Group 2, had BCV Type I colostrum antibody titers above the minimum protective titer. These results indicate that administration of the vaccine at 3 months gestation (6 months prior to parturition) induced an adequate level of protective colostrum antibody titer for the coronavirus fraction.

TABLES

TABLE 1

Antitoxin Titer to *C. perfringens* Type C Beta Toxin in Pooled Sera and Colostrum of Heifers.

| Group | Antitoxin titer (Units/mL) | | |
|---|---|---|---|
| | Prior to vaccination | At the time of calving | Colostrum |
| Control | <1 | <1 | <1 |
| Vaccinate | <1 | 1-5 | 20-25 |

TABLE 2

Antitoxin Titer to *C. perfringens* Type C Beta Toxin in Pooled Sera of Day Old Calves.

| Group | Antitoxin titer (Units/mL) |
|---|---|
| Control | <1 |
| Vaccinate | 5-10 |

TABLE 3

Antitoxin Titer to *C. perfringens* Type D Epsilon Toxin in Pooled Sera and Colostrum of Heifers.

| Group | Antitoxin titer (Units/mL) | | |
|---|---|---|---|
| | Prior to vaccination | At the time of calving | Colostrum |
| Control | <1 | <1 | <1 |
| Vaccinate | <1 | 1-2 | >2 |

TABLE 4

Antitoxin Titer to *C. perfringens* Type D Epsilon Toxin in Pooled Sera of Day Old Calves.

| Group | Antitoxin titer (Units/mL) |
|---|---|
| Control | <1 |
| Vaccinate | 1-2 |

TABLE 5

Mortality in Calves Born to Vaccinated and Control Heifers Following Heterologous Challenge with *E. coli*.

| Group | No. of calves died/Total challenged | % Mortality |
|---|---|---|
| Control | 8/10 | 80 |
| Vaccinate | 3/21 | 14 |

TABLE 6

Antibody Titer to K99 Antigen in Serum and Colostrum of Vaccinated Heifers, Control Heifers, and in Serum of Day Old Calves.

| Group | Heifer Serum Titer | | | | Calf Serum |
|---|---|---|---|---|---|
| | Day 0 | Day 101 | At Calving | Colostrum Titer | Titer After Nursing |
| Vaccinate Group Geometric Mean Titer | 4 | 51 | 27 | 92 | 16 |
| Placebo Control Group Geometric Mean Titer | 4 | 7 | 4 | 9 | 4 |

TABLE 7

BCV Type 1 Serum Neutralization GMT Summary.

| | BCV | | | | | | | |
|---|---|---|---|---|---|---|---|---|
| Group | Pre | 0 DPV1 | 0 DPV2/ 34 DPV1 | 64 DPV1 | 6 Mos. Gest. | 7 Mos Gest. | 8 Mos. Gest. | Day of Calving |
| Group 1 (Vaccinates) | 215 | 244 | 2937 | 4360 | 1017 | 1607 | 1128 | 355 |
| Group 2 (Placebo) | 246 | 237 | 1552 | 873 | 274 | 501 | 391 | 123 |

DPV: Days post vaccination

TABLE 8

BCV Type III Serum Neutralization GMT Summary.

| | BCV | | | | | | | |
|---|---|---|---|---|---|---|---|---|
| Group | Pre | 0 DPV1 | 0 DPV2/ 34 DPV1 | 64 DPV1 | −6 Mos. Gest. | −7 Mos Gest. | −8 Mos. Gest. | Day of Calving |
| Group 1 (Vaccinates) | 236 | 197 | 2195 | 1722 | 867 | 942 | 849 | 516 |
| Group 2 (Placebo) | 214 | 200 | 1152 | 377 | 274 | 370 | 352 | 256 |

DPV: Days post vaccination

TABLE 9

Group Geometric Mean Antibody Titers to BCV Type I.

| Group | Group Geometric Mean Antibody Titer to BCV Type I | Percent of Heifers Showing Antibody Units Above Minimum Protective Level |
|---|---|---|
| Group 1 (Vaccinates) | 7538 | 18/25 = 72% |
| Group 2 (Placebo Controls) | 1039 | 5/24 = 21% |

TABLE 10

Group Geometric Mean Antibody Titers to BCV Type III.

| Group | Group Geometric Mean Antibody Titer to BCV Type III | Percent of Heifers Showing Antibody Units Above Minimum Protective Level |
|---|---|---|
| Group 1 (Vaccinates) | 6517 | 20/25 = 80% |
| Group 2 (Placebo Controls) | 790 | 5/24 = 21% |

What is claimed is:

1. A method for aiding in the prevention of neonatal diarrhea comprising administering a vaccine to a pregnant bovine at about 5 to 7 months prior to parturition; and after parturition, providing a calf with colostrum from the bovine; wherein the vaccine comprises an antigen from a pathogen associated with neonatal diarrhea; and wherein the antigen is selected from the group consisting of an inactivated *Escherichia coli* (*E. coli*) or an extract thereof; an inactivated bovine rotavirus; a bacterin toxoid from *Clostridium perfringens* (*C. perfringens*); and a recombinant *Cryptosporidium* protein.

2. The method of claim 1 wherein the antigen is an inactivated *E. coli* or an extract thereof.

3. The method of claim 2 wherein the extract is a cell-free extract of *E. coli* pilus type K99.

4. The method of claim 1 wherein the antigen is an inactivated bovine rotavirus.

5. The method of claim 4 wherein the vaccine further comprises a second inactivated bovine rotavirus strain; whereby the vaccine comprises two different bovine rotavirus strains.

6. The method of claim 1 wherein the antigen is a bacterin toxoid from *C. perfringens*.

7. The method of claim 6 wherein the bacterin toxoid from *C. perfringens* is from *C. perfringens* types C and D.

8. The method of claim 1 wherein the antigen is a recombinant *Cryptosporidium* protein.

9. The method of claim 1, further comprising administering the vaccine as a booster vaccine 2 to 6 weeks after said administering of the vaccine.

10. The method of claim 1 wherein said administering of the vaccine is performed about 6 months prior to parturition.

11. The method of claim 10, further comprising administering the vaccine as a booster vaccine 2 to 6 weeks after said administering of the vaccine.

12. A method for aiding in the control of neonatal diarrhea comprising administering a vaccine to a pregnant bovine at about 5 to 7 months prior to parturition; and after parturition, providing a calf with colostrum from the bovine; wherein the vaccine comprises an inactivated bovine coronavirus strain.

13. The method of claim 12 wherein the vaccine further comprises a second inactivated bovine coronavirus strain; whereby the vaccine comprises two different bovine coronavirus strains.

14. A method for providing passive immunity against enterotoxemia, comprising administering a vaccine to a pregnant bovine at about 5 to 7 months prior to parturition; and after parturition, providing a calf with colostrum from the bovine; wherein the vaccine comprises a bacterin toxoid from *C. perfringens* types C and D.

15. The method of claim 14 wherein said administering of the vaccine is performed about 6 months prior to parturition.

16. The method of claim 14, further comprising administering the vaccine as a booster vaccine 2 to 6 weeks after said administering of the vaccine.

17. A method for aiding in the prevention of neonatal diarrhea comprising administering a vaccine to a pregnant bovine at about 5 to 7 months prior to parturition; and after parturition, providing a calf with colostrum from the bovine; wherein the vaccine comprises a cell-free extract of *E. coli* pilus type K99, two inactivated bovine coronaviruses, two inactivated rotaviruses, and a bacterin toxoid from *C. perfringens*; types C and D.

18. The method of claim 17 further comprising a recombinant *Cryptosporidium* protein.

19. The method of claim 18 wherein said administering of the vaccine is performed about 6 months prior to parturition.

20. The method of claim 17, further comprising administering the vaccine as a booster vaccine 2 to 6 weeks after said administering of the vaccine.

21. A method for providing passive immunity against neonatal diarrhea, comprising administering a vaccine to a pregnant bovine at about 5 to 7 months prior to parturition; and after parturition, providing a calf with colostrum from the bovine; wherein the vaccine comprises an antigen from a pathogen that has been associated with neonatal diarrhea; and wherein the antigen is selected from the group consisting of an inactivated *Escherichia coli* (*E. coli*) or an extract thereof; an inactivated bovine rotavirus; an inactivated bovine coronavirus; a bacterin toxoid from *Clostridium perfringens* (*C. perfringens*); and a recombinant *Cryptosporidium* protein.

22. A method for aiding in the prevention of neonatal diarrhea while reducing the number of separate occasions a producer is required to assemble cattle comprising administering to a pregnant bovine an effective immunizing amount of a vaccine on the same occasion that the bovine is checked for pregnancy; and after parturition, providing a calf with colostrum from the bovine; wherein the vaccine comprises a cell-free extract of *E. coli* pilus type K99, two inactivated bovine coronaviruses, two inactivated rotaviruses, and bacterin toxoid from *C. perfringens* types C and D; and wherein the number of separate occasions a producer is required to assemble the cattle is reduced.

23. The method of claim 22 further comprising a recombinant *Cryptosporidium* protein.

24. The method of claim 22, further comprising administering the vaccine as a booster vaccine 2 to 6 weeks after said administering of the vaccine.

* * * * *